United States Patent [19]

Newman

[11] Patent Number: 4,942,883
[45] Date of Patent: Jul. 24, 1990

[54] DRUG DELIVERY DEVICE

[76] Inventor: Martin H. Newman, 77 Norwood St., Sharon, Mass. 02067

[21] Appl. No.: 102,540

[22] Filed: Sep. 29, 1987

[51] Int. Cl.$^5$ .............................................. A61N 1/30
[52] U.S. Cl. ..................... 128/798; 604/20; 424/449
[58] Field of Search ............... 128/798, 799, 801, 803; 604/20; 424/449

[56] References Cited

U.S. PATENT DOCUMENTS

| 3,163,166 | 12/1964 | Brant et al. | 604/20 X |
| 3,289,671 | 12/1966 | Troutman et al. | 604/20 X |
| 4,474,570 | 10/1984 | Ariora et al. | 128/798 X |
| 4,539,996 | 9/1985 | Engel | 128/798 X |
| 4,764,164 | 8/1988 | Sasaki | 604/20 X |

FOREIGN PATENT DOCUMENTS

| 60452 | 9/1982 | European Pat. Off. | 604/20 |
| 8607268 | 12/1986 | Int'l Pat. Institute | 604/20 |
| 8607269 | 12/1986 | Int'l Pat. Institute | 604/20 |

Primary Examiner—Max Hindenburg
Assistant Examiner—J. P. Lacyk
Attorney, Agent, or Firm—Robert F. O'Connell

[57] ABSTRACT

A transdermal medication delivery system in which a housing includes a power source for supplying programmed current pulses to an electrical current path which includes an electrically charged medication and a body location at which the medication is placed. The level of the current pulses and the time over which they are provided is controlled to deliver a predetermined dosage of the medication to the body location at a predetermined rate.

5 Claims, 2 Drawing Sheets

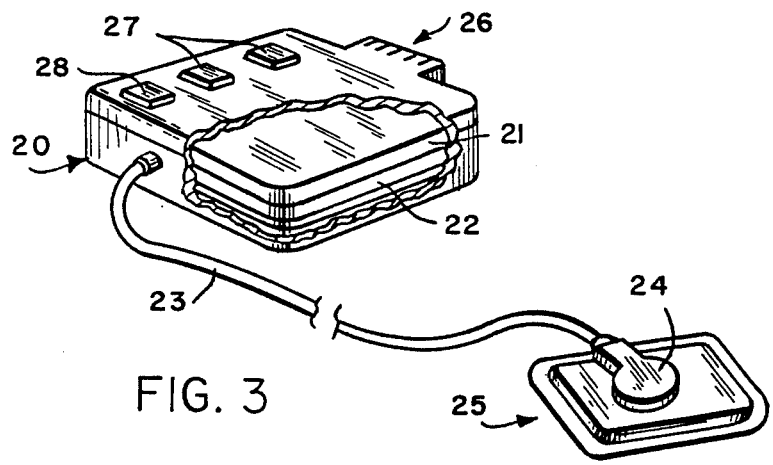
FIG. 3
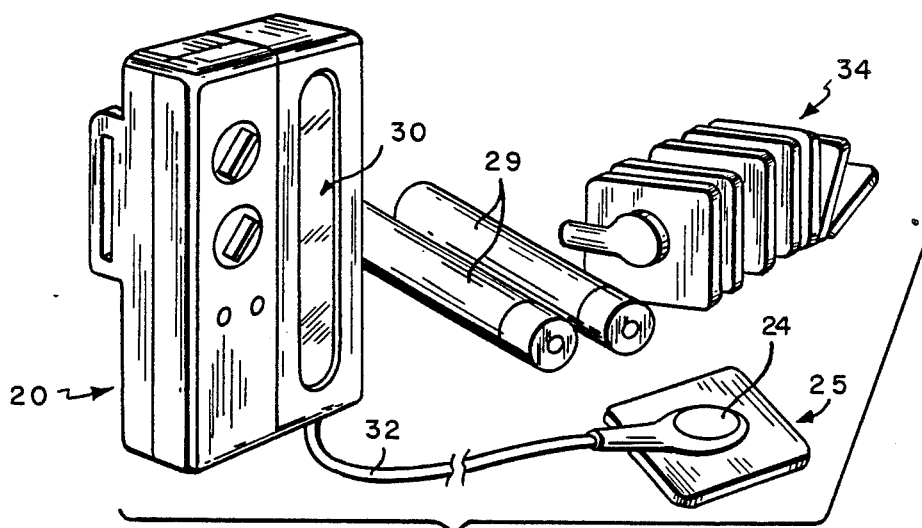
FIG. 4
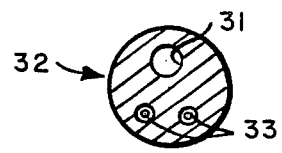
FIG. 4A
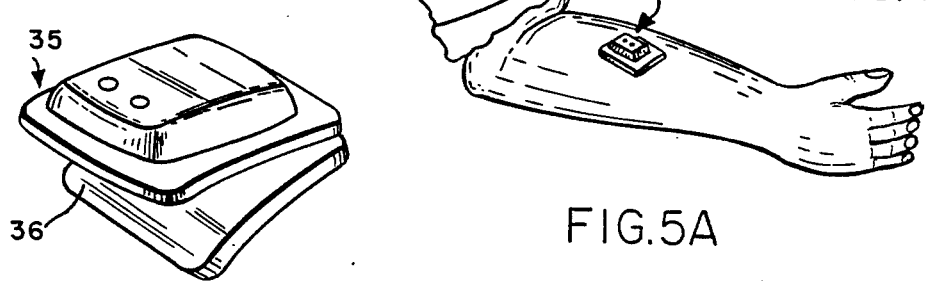
FIG. 5
FIG. 5A

DRUG DELIVERY DEVICE

INTRODUCTION

This invention relates generally to drug delivery systems and, more particularly, to iontophoresis delivery systems in which the components required therefor are preferably contained within the same housing unit and can be tailored in their operations for a specific drug delivery application.

BACKGROUND OF THE INVENTION

Drug delivery systems which use iontophoresis techniques have been proposed over the years. One such system is described, for example, in my pending application, Ser. No. 051,079, filed on May 15, 1987 and entitled "Drug Delivery Systems". The system discussed therein uses a housing unit which includes a microprocessing system for controlling a separately housed programmable power supply which supplies d-c electrical current pulses to an electrode structure containing a medication, or drug, to be delivered to a selected body location of a patient, e.g., transdermally. The electrode is connected to the power supply unit via a cable and the microprocessing system can respond to information concerning a large variety of drugs so as to calculate the drug delivery rate for any particular predetermined identifiable drug and to control the rate of delivery of such drug automatically. The microprocessing system is generalized in its operation so as to control the delivery of a large variety of medications and the housing is designed to include a display means, alarm circuitry, and a card reading system for permitting the identification of a particular drug when the system is to be put into operation. While somewhat portable in nature, the system is normally intended essentially for use in a hospital environment, or in a doctor's office, for example, and cannot be readily carried about or used by a patient outside such environment during the patient's normal activities.

It is desirable, however, in some cases, to make available to a patient a complete drug delivery system which is capable of being carried by, or suitably attached to, the patient and used by the patient even when performing normal activities. It is further desirable that such a system be arranged to deliver a particular drug in a controlled manner automatically once it has been so attached, without in many cases the patient needing to be constantly aware at all of its operation.

BRIEF SUMMARY OF THE INVENTION

The invention in one preferred embodiment thereof comprises a single housing unit which includes a complete drug delivery device which includes a microprocessor, a power source, and a drug containing membrane all within such housing and appropriately interconnected therein. The microprocessor is pre-programmed to control the rate of delivery of the particular drug which is contained in such membrane.

The unit in one preferred embodiment is arranged to be suitably secured to the patient's skin at the body location at which the drug is to be delivered. One or more appropriate sensing means are contained within the housing to provide appropriate information to the microprocessor so as to control the starting and stopping of the operation of the drug delivery system and so as to provide control of the current level supplied by the power source during operation to assure that the drug is being delivered at the desired rate. The structure in a particularly preferred embodiment is, in effect, tailored in its operation specifically to the drug which is being delivered and to the patient for whom the drug is to be used, the delivery rate having been predetermined for the particular patient to whom the particular drug is to be delivered. It is sufficiently compact in form so that, when it is secured to the patient during use, it can be worn during the patient's normal activities and can operate automatically without the patient's needing to be aware of its presence.

DESCRIPTION OF THE INVENTION

The invention can be described with the help of the accompanying drawings wherein FIG. 1 shows a side view, partially in section, of a particular embodiment of the invention;

FIG. 3 shows a perspective view of an alternative embodiment of the invention;

FIG. 4 shows a perspective view of a further alternative embodiment of the invention;

FIG. 4A shows a cross-section view of the cable of FIG. 4;

FIGS. 5 and 5A show perspective views of a still further alternative embodiment of the invention.

Figure 1:
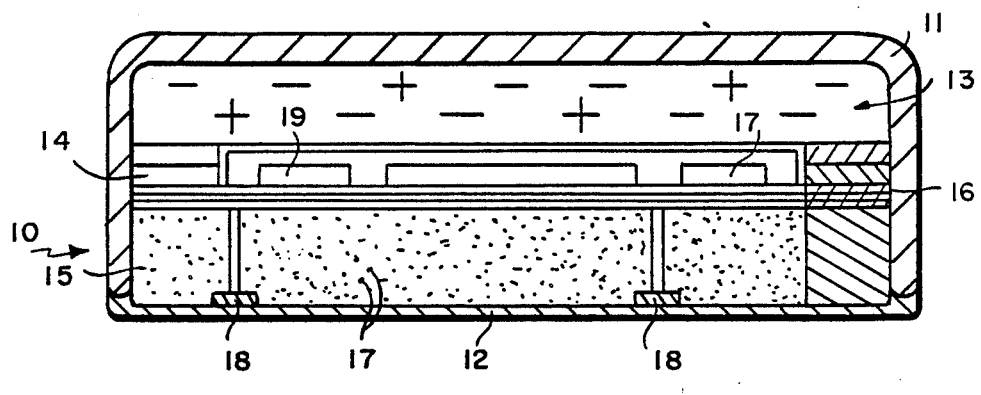
Figure 2:
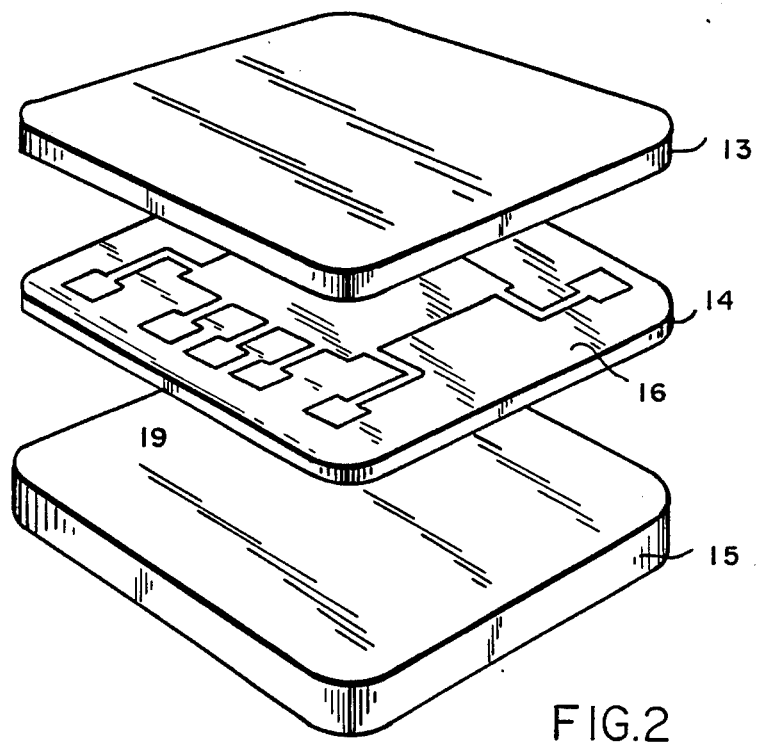
FIG. 2 shows an exploded perspective view of portions of the embodiment depicted in FIG. 1.

As can be seen in FIGS. 1 and 2, the drug delivery device 10 in accordance with one particular embodiment of the invention comprises a housing which i® formed with an upper dome-like protective cover 11 and a flexible bottom element 12. Cover 11 is generally rigid, or semi-rigid, in nature and can be made of any suitable material, preferably a relatively light substance such as a suitable dielectric plastic material. The flexible element 12 can be a thin plastic strip which fits over the lower opening of cover 11 and has an adhesive material at its periphery which permits it to be adhered to the lower edge of cover 11.

The housing encases three main sections in the preferred embodiment depicted, such sections being in effectively layered positions therein, identified in both FIGS. 1 and 2 as a power supply section 13, to processor section 14 and a drug/membrane section 15. Power supply section 13 in a preferred embodiment comprises a lithium battery which produces a d-c voltage for providing a d-c current through drug membrane 15 as well as through at least a portion of a body location at which the drug is to be delivered. The d-c current is applied, for example, in the form of d-c current pulses, the amplitudes of which are predetermined so that a particular drug is delivered at the desired dosage rate. The drug molecules when electrically charged have a particular polarity for each specific drug which is selected for delivery and the polarity of the current pulses which are applied thereto is preselected to have the polarity produce the required iontophoretic operation.

Microprocessor section 14 includes a suitable microprocessor chip and one or more associated memory chips mounted on a printed circuit substrate, or board, 16. Connections among the battery, the microprocessor and memory chips, and one or more sensors, which are discussed in more detail below, as well as a plurality of user activated, electrically conductive paths are provided by a plurality of conductive paths in the printed circuit board fabricated in a manner well known to the art.

Drug/membrane section 16 comprises a carrier of a porous or non-porous, preferably hydrophilic, material having molecules 17 of a drug distributed throughout. The drug molecules are initially in a non-charged state and can be converted to a charged state by the application of a suitable fluid, e.g., few drops of water, to the carrier which ionizes the molecules so that they have a polarity depending on the particular drug involved as selected during the manufacture thereof.

One or more sensors 18 may be positioned at the lower surface of the carrier. When the flexible strip 12 is removed the carrier surface and the sensors can be positioned against the patient's skin at a body location where the drug is to be delivered. Sensors 18 may be in the form of temperature sensors (e.g., thermistors), pulse rate sensors (capacitance sensing elements), pressure transducers, or the like, as may be desired for any particular application. The outputs from sensors 18 are supplied to the printed circuit board for us by the microprocessor as desired.

The device shown in FIGS. 1 and 2 can be designed so that it is tailor-made for providing delivery of a specified drug at a specified dosage rate which can be predetermined for an average patient. Accordingly, once the particular drug is selected the dosage rate (i.e.. the total time for delivery of the total amount of drug being used) is predetermined in accordance with the manufacturer's specifications. Using such predetermined delivery time, the d-c current level required for delivery at such dosage rate can be determined. As long as such d-c current level is below the current sensitivity level which is determined to be tolerable by the average patient, the microprocessor can be provided with a fixed, predetermined program for providing d-c current pulses at such current level to permit the predetermined rate of delivery during use.

Once the drug delivery time and the desired current level have been predetermined, the microprocessor program controls the supplying of current pulses from the lithium battery (or other appropriate d-c power source) at such level during operation. The microprocessor controls the output level from the power source, preferably so as to supply square wave pulses, for example, at a preselected pulse repetition rate, or frequency. Preferably, the frequency rate can be set at 50 KHz. which tends to avoid interference with other electronic equipment which may be in the vicinity of the user. Current levels for delivery of drugs by devices in accordance with the invention are generally found to be in ranges up to 5.0 mA. et voltages up to 35 volts d-c. However, such current levels may vary depending upon the particular drug being administered and upon other conditions, including the voltage level, the type of patient, etc. Appropriately coded information is entered into the microprocessor prior to manufacture of the self-contained device via suitable programmable pad entry keys 19 as are well known in the art. Once such values are entered, the pre-programmed microprocessor, when actuated, automatically controls the supplying of current pulses at the desired level for the delivery time which has been so entered for the particular drug.

In the embodiment depicted in FIGS. 1 and 2 the start of drug delivery can be initiated by a suitable switch (not shown) and/or in response to an appropriate sensor output, and the delivery halted automatically at the end of the delivery time or at some time prior thereto in response to a sensor output. If desired, suitable indicator lights, for example, can also be positioned on the housing to indicate when the system is on, to indicate that the system has been stopped prior to complete drug delivery, to indicate that drug delivery is complete, etc., as desired. Thus, the overall device provides a complete, self-contained package which, when secured to a patient, automatically provides drug delivery at the preset dosage rate until delivery is complete. The user has no control over such rate of delivery other than to initiate delivery or to remove the device from the body location at which it has been placed. Once drug delivery is complete, the device can be discarded and a new device secured at the desired location if further delivery of the drug is prescribed.

As an alternative embodiment of the invention, delivery of different drugs, using the same power source and microprocessor control can also be achieved, as shown in FIG. 3, using a disposable drug containing pad. As seen therein, a housing 20 completely encases a battery 21 and a microprocessor board 22, d-c current pulses being supplied via a cable 23 to an electrode 24 which supplies such current pulses to a drug delivery pad, or patch, 25 which contains a drug to be delivered to a body location to which it is secured. The electrode is arranged to accept a number of drug delivery patches containing different drugs. In this embodiment, information concerning the identity of the drug, the dosage rate, the time of drug delivery, and whatever sensed parameter values are required to control drug delivery are entered by a user into the microprocessor system by the use of a plurality of programmable pads 26, or by a card, or tape (not shown). In addition, the patient may be permitted to control the starting or stopping of drug delivery by the use of suitable patient control pads 27, which can be used to override an automatically predetermined drug delivery program which has been implemented in the microprocessor. Moreover, an indicator light 28 may be used to show a user when drug delivery is occurring.

In the system of FIG. 3, only the drug patch need be discarded after delivery of the drug and the control device can be retained so that new parameters can be entered for the delivery of a different drug.

As a further alternative embodiment of the invention, the patch member 25 can be one which comprises a carrier which has no drug contained therein but which is capable of having a drug supplied thereto. As shown in FIG. 4, for example, a drug cartridge 29 can be used to store a predetermined dosage of a drug, which cartridge can be inserted into an opening 30 of a housing unit 20. Once inserted the drug is delivered to the patch member 25 via a suitable tube, or lumen, 31 enclosed in an overall cable structure 32 together with the electrical wires 33 which are used to carry the d-c current pulses, as shown in FIG. 4A. Suitable information concerning each drug can be entered into a microprocessor control system positioned within housing 20, as discussed above so as to permit control of the delivery. The drug within cartridges 29 can be in liquid form, wherein the drug is already ionized and supplied to a porous carrier within drug patches 34 for the delivery operation. Alternatively, prepackaged drug patches 34, each already containing drug molecules in a carrier, can be attached to electrode 24 without the need to use cartridges 29.

A still further alternative of the invention is shown in FIG. 5, wherein a housing 35 includes a power supply source and microprocessor control system as discussed above. Housing 35 is arranged so that flexible and disposable patches 36 comprising a carrier containing a drug to be delivered can be suitably attached to the open underside of housing 35. Such patches are readily removable once the drug contained therein has been delivered. When the drug patch has been so attached, information concerning the dosage rate (drug delivery time) and other required parameters for the known dosage therein can be entered into the microprocessor control system as discussed above and the overall device suitably secured to the skin at a body location to which the drug is to be delivered as shown in FIG. 5A. When delivery is complete, the disposible drug patch 36 can be removed end discarded and a new patch attached to housing 35. Thus, the need for a cable and electrode structure, as discussed with reference to FIG. 4, can be eliminated and the control and power supply system can be retained and only the drug patch itself need be disposed.

Other embodiments and modifications thereto within the spirit and scope of the invention will occur to those in the art upon reading and considering this disclosure and, hence, the invention is not to be construed as necessarily limited to only the particular embodiments discussed above, except as defined by the appended claims.

What is claimed is:

1. A self-contained transdermal medication delivery system for delivering a pre-specified medication to a body location comprising a housing containing at least a source of electrical current pulses;

microprocessor control means for automatically providing said current pulses in accordance with a fixed, predetermined program established in said microprocessor control means prior to manufacture of said system for controlling the level of said current pulses and the time period over which said pulses are to be provided;

means for retaining said pre-specified medication, being electrically charged, for placement at a body location for forming with said body location an electrical current path responsive to said current pulses to cause said medication to be delivered transdermally from said medication retaining means to said body location;

said microprocessor means thereby permitting a predetermined dosage of said pre-specified medication to be delivered automatically at a predetermined rate to said body location in accordance with said fixed, predetermined program wherein said medication retaining means is formed separately from said housing and includes a hydrophilic membrane having molecules of a medication distributed therein, and further including electrode means for coupling to said separately formed medication retaining means;

cable means for interconnecting said electrode means and said source of current pulses, one or more separately formed cartridges containing medication in liquid form, each cartridge being inserted into said housing means for attachment to said cable means, said cable means including a channel for transporting said liquid medication to the membrane of said medication retaining means for distribution of said medication therein.

2. A transdermal medication delivery system in accordance with claim 1 wherein said control means includes means for permitting a user of said system manually to start and/or stop the delivery of said medication to said body location.

3. A transdermal medication delivery system in accordance with claim 1 wherein said housing further contains at least one sensor means for sensing a selected body characteristic at said body location, said control means being responsive to the sensed body characteristic from said sensor means for controlling the starting and/or stopping of the delivery of said medication to said body location.

4. A transdermal medication delivery system in accordance with claim 1 wherein said source of current pulses is a lithium battery.

5. A transdermal medication delivery system in accordance with claim 1 wherein said cartridge contains a predetermined dosage of a specified medication.

* * * * *